US008329674B2

(12) United States Patent
Yang et al.

(10) Patent No.: US 8,329,674 B2
(45) Date of Patent: Dec. 11, 2012

(54) FILM FORMING DENTAL COMPOSITIONS AND RELATED METHODS

(75) Inventors: Jie Yang, Woodbury, MN (US); Bhaskar V. Velamakanni, Woodbury, MN (US); Sumita B. Mitra, West St. Paul, MN (US); Alphonsus V. Pocius, Maplewood, MN (US); John J. Stofko, Jr., St. Paul, MN (US); Jeremy M. Yarwood, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 314 days.

(21) Appl. No.: 12/594,988

(22) PCT Filed: Jul. 10, 2008

(86) PCT No.: PCT/US2008/069628
§ 371 (c)(1),
(2), (4) Date: Oct. 7, 2009

(87) PCT Pub. No.: WO2009/014905
PCT Pub. Date: Jan. 29, 2009

(65) Prior Publication Data
US 2010/0130445 A1 May 27, 2010

Related U.S. Application Data

(60) Provisional application No. 60/951,758, filed on Jul. 25, 2007.

(51) Int. Cl.
| | | |
|---|---|---|
| A01N 43/04 | (2006.01) | |
| A61K 31/70 | (2006.01) | |
| C08B 37/00 | (2006.01) | |
| C07H 11/04 | (2006.01) | |
| C07H 13/00 | (2006.01) | |
| C07H 11/00 | (2006.01) | |
| C07H 13/12 | (2006.01) | |

(52) U.S. Cl. ............ 514/62; 536/114; 536/117; 536/118
(58) Field of Classification Search ........................ None
See application file for complete search history.

(56) References Cited

U.S. PATENT DOCUMENTS

| | | |
|---|---|---|
| 4,871,786 A | 10/1989 | Aasen et al. |
| 5,130,347 A | 7/1992 | Mitra |
| 5,362,480 A | 11/1994 | Au et al. |
| 5,438,076 A | 8/1995 | Friedman |
| 5,468,477 A | 11/1995 | Kumar et al. |
| 5,525,648 A | 6/1996 | Aasen et al. |
| 5,607,663 A | 3/1997 | Rozzi et al. |
| 5,624,906 A | 4/1997 | Vermeer |
| 5,662,887 A | 9/1997 | Rozzi et al. |
| 5,725,882 A | 3/1998 | Kumar et al. |
| 5,866,630 A | 2/1999 | Mitra et al. |
| 5,871,714 A | 2/1999 | Budny |
| 5,876,208 A | 3/1999 | Mitra et al. |
| 5,888,491 A | 3/1999 | Mitra et al. |
| 6,312,668 B2 | 11/2001 | Mitra et al. |
| 6,620,405 B2 | 9/2003 | Oxman et al. |
| 7,223,826 B2 | 5/2007 | Ali et al. |
| 2002/0136768 A1 | 9/2002 | Staats |
| 2003/0099602 A1 | 5/2003 | Levin et al. |
| 2003/0108611 A1 | 6/2003 | Bosch |
| 2003/0114553 A1 | 6/2003 | Karim et al. |
| 2003/0129144 A1 | 7/2003 | Scott |
| 2003/0175367 A1 | 9/2003 | Mao |
| 2004/0147595 A1 | 7/2004 | Kjelleberg et al. |
| 2004/0151691 A1 | 8/2004 | Oxman et al. |
| 2004/0185013 A1 | 9/2004 | Burgio et al. |
| 2005/0058744 A1 | 3/2005 | Steinberg et al. |
| 2005/0265948 A1 | 12/2005 | Ridley et al. |
| 2005/0281773 A1 | 12/2005 | Wieland et al. |

FOREIGN PATENT DOCUMENTS

| | | |
|---|---|---|
| DE | 4406746 | 9/1995 |
| EP | 0 057 323 | 5/1983 |
| EP | 0945119 | 9/1999 |
| JP | 55069506 | 5/1980 |
| JP | 09-509666 | 9/1997 |
| JP | 2005-029484 | 3/2005 |
| WO | WO 94/24097 | 10/1994 |
| WO | WO 02/30380 | 4/2002 |
| WO | WO 2006/029893 | 3/2006 |
| WO | WO 2007/079069 | 7/2007 |
| WO | WO 2008/033911 | 3/2008 |
| WO | WO 2009/014907 | 1/2009 |

OTHER PUBLICATIONS

Crane et al., "Isonucleosides from Glucosamine," Journal of Carbohydrates Nucleosides Nucleotides, 7(5), 281-296 (1980).*
Rudnic et al., "Oral Solid Dosage Forms," Chapter 89 in Remington's Pharmaceutical Sciences, 18th Edition, Gennaro et al (eds.), Mack Publishing Co., Easton, PA, 1990, see in particular pp. 1635-1636 ("Binders").*
International Search Report PCT/US2008/069628, Dec. 30, 2008.
Homer KA et al., Effects of N-acetylglucosamine on carbohydrate germentation by *Streptococcus mutans* NCTC 10449 and *Streptococcus sobrinus* SL-1, Infect Immun. Jan. 1993, vol. 61, No. 1, pp. 295-302.
A.F. Paes Leme, H. Koo, C.M. Bellato, G. Bedi, and J.A. Cury (2006), The Role of Sucrose in Cariogenic Dental Biofilm Formation—New Insight, J. Dent. Res., 85(10), 878-887.
M. Fontana, and D.T. Zero (2006), Assessing Patients' Caries Risk, JADA, 137(9), 1231-1239.
M. Marotta, A. Martino, A. De Rosa, E. Farina, M. Carteni, M. De Rosa (2002), Degradation of dental plaque glucans and prevention of glucan formation using commercial enzymes, Process Biochemistry, 38, 101-108.
M. Inoue, T. Yakushiji, M. Katsuki, N. Kudo and T. Koga (1988), Reduction of the adherence of *Streptococcus sobrinus* insoluble α-D-glucans by endo-(1,3)-α-D-glucanase. Carbohydrate Research, 182, 277-286.
D. Kim, R. Su-jin, H. Soo-jin, K. Do-won and K.J. Ho-sang (1999), Characterization of a novel carbohydrase from *Lipomyces starkeyi* KSM22 for dental application. Microbiol Biotechnol, 9(3), 260-264.
C.F. Schechtele, R.H. Staat and S.K. Harlander (1975), Dextranases from oral bacteria: inhibition of water-insoluble glucan production and adherence to smooth surfaces by *Strptococcus* mutans. Infect Immun. 12(2), 309-317.

(Continued)

*Primary Examiner* — Lawrence E Crane
(74) *Attorney, Agent, or Firm* — Nicole J. Einerson

(57) ABSTRACT

Film forming dental compositions comprising a compound of formula (I) or a pharmaceutically acceptable salt thereof, and a binder. The film forming dental compositions can include an amino sugar, a derivative of an amino sugar, or a pharmaceutically acceptable salt thereof, and can be useful in inhibiting biofilm formation in an oral cavity.

15 Claims, No Drawings

OTHER PUBLICATIONS

S. Hamada, J. Mizuno, Y. Murayama, T. Ooshima and N. Masuda, S. Sobue (1975), Effect of dextranase on the extracellular polysaccharide synthesis of *Streptococcus mutans*: Chemical and Scanning Electron Microscopy SStudies, Infect Immun, 12(6), 1415-1425.

P.E. Kolenbrander and R.N. Andersen (1989), Infect. Immun., Inhibition of Coaggregation between *Fusobacterium nucleatum* and *Porphyromonas* (*Bacteroides*) *gingivalis* by Lactose and Related Sugars; 57, 3204-3209.

B. Shaniztki, D. Hurwitz, N. Smorodinsky, N. Ganeshkumar and E.I. Weiss (1997), Infect. Immun. Identification of a *Fusobacterium nucleatum* PK1594 Galactose-Binding Adhesin Which Mediates Coaggregation with Periopathogenic Bacteria and Hemagglutination; 65, 5231-5237.

R.J. Gibbons, J.V. Qureshi (1979), Infection and Immunity, Inhibition of Adsorption of *Streptococcus mutans* Strains to Saliva-Treated. Hydroxyapatite by Galactose and Certain Amines; 26(3), 1214-1217.

Oral Health in America: A Report of the Surgeon General, Executive Summary (2000), Rockville, MD; U.S. Natl. Inst. Of Dental and Craniofacial Research, 332 pages.

S. Imazato, M. Torii, Y. Tscuchitani, J.F. McCabe, and R.R.B. Russell (1994), Incorporation of Bacterial Inhibitor into Resin Composite, J. Dent. Res.; 73(8); 1437-1443.

MSDS for Carbomer 910, 934, 934p, 940, 941, downloaded from the internet on Feb. 12, 2012, <http://www.sciencelab.com/msds.php?msdsID=9925741> 5 pgs.

Bakri et al., "Inhibitory effect of garlic extract on oral bacteria", Archives of Oral Biology (2005) 50, 645-651.

Park et al, "Characteristics of Different Molecular Weight Chitosan Films Affected by the Type of Organic Solvents", Journal of Food Science, vol. 67, Nr. 1, (2002) 194-197.

* cited by examiner

FILM FORMING DENTAL COMPOSITIONS AND RELATED METHODS

CROSS-REFERENCE TO RELATED APPLICATIONS

This application is a national stage filing under 35 U.S.C. 371 of PCT/US2008/069628, filed Jul. 10, 2008, which claims priority to U.S. Provisional Patent Application No. 60/951,758 filed Jul. 25, 2007, the entire disclosure of which is incorporated herein by reference.

TECHNICAL FIELD

The present disclosure relates to dental compositions, and more specifically, to film forming dental compositions and methods to inhibit biofilm formation in the oral cavity of a subject.

BACKGROUND

Dental plaque, which may include bacteria such as *Streptococcus mutans*, comprises a biofilm that forms on surfaces in the oral cavity. Dental plaque is at least partly responsible for dental caries, gingivitis, and periodontal diseases. Bacteria in dental plaque metabolize carbohydrates (for example, simple sugars) in the mouth and produce acids that can etch tooth enamel. The dentin thus exposed can then be colonized by bacteria. Dental plaque can serve as a substrate for the deposition of tartar or calculus. Build up of calculus can lead to gingivitis and, ultimately, to periodontal disease. A currently available method to remove dental plaque from teeth is mechanical removal with, for example, dental floss or a toothbrush. A toothbrush can aid in removing dental plaque from exposed surfaces of a tooth, and dental floss can aid in removing dental plaque from, for example, interproximal and subgingival surfaces. Proper and regular use of dental floss and a toothbrush can mechanically remove or reduce dental plaque, and can reduce the incidence of dental caries, gingivitis, and periodontal disease. Certain antimicrobial formulations are available (in the form of mouthwashes, rinses, and toothpastes, for example) to aid in the control and treatment of dental plaque, dental caries, gingivitis, and periodontal disease.

SUMMARY

As noted above, proper and regular use of dental floss and a toothbrush can reduce dental plaque and the incidence of dental caries. However, dental floss and a toothbrush are not always used properly and regularly. Moreover, a biofilm matrix such as dental plaque may contribute to the isolation of bacteria from the protective effect of antimicrobial compounds and, thus, may interfere with the function of antimicrobial formulations such as mouthwashes, rinses, and toothpastes. As a result, alternative methods to control or prevent dental plaque, rather than to mechanically remove it, are desirable. Thus, we recognize that there is a need for compositions and methods to inhibit the formation of biofilms, particularly in the oral cavity.

In one aspect, the present invention provides a dental composition comprising a) at least one compound of Formula I or a pharmaceutically acceptable salt thereof:

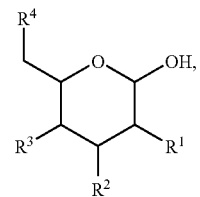

(I)

wherein $R^1$, $R^2$, and $R^3$ are independently selected from the group consisting of OH and $NR^5R^6$; $R^4$ is selected from the group consisting of OH, $OP(O)(OH)_2$, $OSO_3H$, and $NR^5R^6$; $R^5$ and $R^6$ are independently selected from the group consisting of a hydrogen atom, an alkyl group, $C(O)R^7$, and $SO_2R^8$; $R^7$ and $R^8$ are independently selected from the group consisting of an alkyl group, an aryl group, and an aralkyl group; provided that at least one of $R^1$, $R^2$, $R^3$, and $R^4$ is $NR^5R^6$; and b) a binder. In some embodiments, the dental composition is a film forming dental composition. The dental composition may be in a form of a solution, a dispersion, a suspension, an emulsion, a solid, a paste, a foam, or a gel. In some embodiments, the dental composition comprises a pharmaceutically acceptable salt having at least one counter ion selected from an inorganic anion, an organic anion, and combinations thereof. In some embodiments, the counter ion is selected from fluoride, chloride, bromide, iodide, sulfate, tetraarylborate, tetrafluoroborate, carbonate, phosphate, acetate, benzoate, fumarate, maleate, tartrate, ascorbate, benzenesulfonate, toluenesulfonate, citrate, and combinations thereof.

In some embodiments, $NR^5R^6$ may be an amino group, in which $R^5$ and $R^6$ are independently selected from the group consisting of a hydrogen atom and an alkyl group. In some embodiments, $NR^5R^6$ may be a carboxamido or a sulfonamido group, in which $R^5$ is $C(O)R^7$ or $SO_2R^8$, respectively, and $R^6$ is a hydrogen atom or an alkyl group. In certain embodiments, $R^5$ is $C(O)R^7$ or $SO_2R^8$, and $R^6$ is an alkyl group having about one to about twenty carbon atoms. In some embodiments, $NR^5R^6$ may be a carboximido group, in which $R^5$ and $R^6$ are each $C(O)R^7$. In some embodiments, $NR^5R^6$ may be a sulfonimido group, in which $R^5$ and $R^6$ are each $SO_2R^8$. In certain embodiments, $R^5$ may be $C(O)R^7$ and $R^6$ may be $SO_2R^8$. In various embodiments, $R^7$ and $R^8$ are independently selected from the group consisting of an alkyl group, an aryl group, and an aralkyl group. In some embodiments, $R^4$ is a phosphate ester group, $OP(O)(OH)_2$. In other embodiments, $R^4$ is a sulfate ester group, $OSO_3H$. In some embodiments, $R^1$ is $NR^5R^6$. When $R^1$ is $NR^5R^6$, $R^5$ and $R^6$ may independently be selected from the group consisting of a hydrogen atom and an alkyl group, $R^2$ and $R^3$ may be OH, and $R^4$ may be either OH, or $OP(O)(OH)_2$. In some embodiments, $R^2$, $R^3$, and $R^4$ are OH.

The dental composition may be a therapeutic dental composition. The dental composition is a biofilm inhibiting composition, i.e., it is useful for inhibiting the formation of biofilms. The composition is particularly useful for inhibiting the formation of dental plaque, and more particularly for inhibiting the formation of dental plaque in an oral cavity of a subject.

The binder component of the composition can comprise any polymer, including a film forming polymer. The binder component may comprise at least one of an addition polymer and a condensation polymer. In some embodiments, the binder may be an acrylic polymer, a vinyl polymer, an epoxy polymer, a polyurea, a polyester, a polyanhydride, a polyurethane, or combinations thereof. Typically, the binder comprises an acrylic polymer, i.e., a polymer formed by polymerization or copolymerization of at least one ester of acrylic acid or methacrylic acid.

In certain implementations of the invention, the dental composition may further comprise a pharmaceutically acceptable carrier such as ethanol. In one embodiment, the carrier comprises water. In addition, the dental composition may optionally comprise a flavoring agent, a coloring agent, or both.

In another aspect, the invention provides a method of inhibiting biofilm formation on a surface of the oral cavity of a subject, comprising the steps of (1) providing a composition comprising a compound of Formula I or a pharmaceutically acceptable salt thereof, and a binder, wherein the composition is a film forming composition, and (2) applying the composition to a surface in the oral cavity of a subject. Typically, the subject is a human or a non-human animal or mammal. The applying step may include immersing inserting, rinsing, spraying, brushing, swabbing, or combinations thereof. The method can include, in some embodiments, applying the composition to a hard surface (e.g., a tooth) in the oral cavity.

In yet another aspect, the invention provides a kit comprising (1) a composition comprising a compound of Formula I or a pharmaceutically acceptable salt thereof, and a binder, wherein the composition is a film forming composition, and (2) an application accessory. The application accessory can be a container, a sprayer, a brush, a swab, a tray, or combinations thereof.

This summary is not intended to describe each and every embodiment or implementation of the present invention. Further embodiments, features, and advantages of the present invention will be apparent from the following detailed description thereof and from the claims.

DETAILED DESCRIPTION

In several places throughout the application, guidance is provided through lists of examples, which examples can be used in various combinations. In each instance, the recited list serves only as a representative group and should not be interpreted as an exclusive list.

As used herein,

The terms "comprises" and variations thereof do not have a limiting meaning where these terms appear in the description and claims;

Any recitation of numerical ranges by endpoints includes all numbers subsumed within that range (e.g., 1 to 5 includes 1, 1.5, 2, 2.75, 3, 3.80, 4, 5, etc.);

The terms "a," "an," "the," "at least one," and "one or more" are used interchangeably. Thus, for example, a composition that comprises "a" compound of Formula I can be interpreted to mean that the composition includes "one or more" compounds of Formula I;

The term "dental composition" refers to a composition for use in the oral cavity of a subject;

The term "binder" refers to a polymeric or oligomeric binder compound;

The term "film forming" refers to a property of a compound, binder, polymer, or composition wherein the compound, binder, polymer, or composition is in the form of a substantially continuous film when substantially free of solvent or carrier;

The term "therapeutic" refers to preventing, ameliorating, treating, improving, or curing a disease or condition;

The term "biofilm" refers to a matrix comprising bacteria;

The term "biofilm inhibiting" refers to limiting the formation or growth of a biofilm;

The term "acrylic polymer" refers to a polymer formed by polymerization or copolymerization of at least one ester of acrylic acid or methacrylic acid;

The term "hard surface" refers to a surface in the oral cavity comprising hard material, such as bone, dental enamel, dentin, and dental restorations; and The term "dental restorations" refers to fillings, inlays, onlays, veneers, temporary and permanent crowns or bridges, implants, or orthodontic devices such as brackets or archwires.

In one aspect, the dental composition of the invention comprises a compound of Formula I or a pharmaceutically acceptable salt thereof:

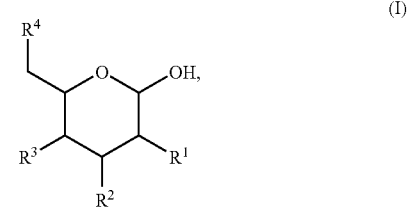

(I)

wherein $R^1$, $R^2$, and $R^3$ are independently selected from the group consisting of OH and $NR^5R^6$; $R^4$ is selected from the group consisting of OH, $OP(O)(OH)_2$, $OSO_3H$, and $NR^5R^6$; $R^5$ and $R^6$ are independently selected from the group consisting of a hydrogen atom, an alkyl group, $C(O)R^7$, and $SO_2R^8$; $R^7$ and $R^8$ are independently selected from the group consisting of an alkyl group, an aryl group, or an aralkyl group; provided that at least one of $R^1$, $R^2$, $R^3$, and $R^4$ is $NR^5R^6$.

It is recognized that the compounds of Formula I comprise chiral carbon atoms. For simplicity, in Formula I the stereochemical configuration about each of the chiral carbon atoms is not specified. It is intended that Formula I, as used in this description and in the claims, represents each of the compounds having any of the possible stereochemical configurations.

In Formula I, at least one of $R^1$, $R^2$, $R^3$, and $R^4$ is $NR^5R^6$. $R^1$, $R^2$, and $R^3$ are independently selected from the group consisting of OH and $NR^5R^6$. Each of $R^1$, $R^2$, and $R^3$ may be OH, any two of $R^1$, $R^2$, and $R^3$ may be OH, or any one of $R^1$, $R^2$, and $R^3$ may be OH. Each of $R^1$, $R^2$, and $R^3$ may be $NR^5R^6$, any two of $R^1$, $R^2$, and $R^3$ may be $NR^5R^6$, or any one of $R^1$, $R^2$, and $R^3$ may be $NR^5R^6$. $R^4$ is selected from the group consisting of OH, $OP(O)(OH)_2$, $OSO_3H$, and $NR^5R^6$. In some embodiments, $R^4$ is OH. In other embodiments, $R^4$ is $OP(O)(OH)_2$. In other embodiments, $R^4$ is $OSO_3H$. In other embodiments, $R^4$ is $NR^5R^6$.

$R^5$ and $R^6$ are independently selected from the group consisting of a hydrogen atom, an alkyl group, $C(O)R^7$, and $SO_2R^8$. Each of $R^5$ and $R^6$ may be a hydrogen atom, each of $R^5$ and $R^6$ may be an alkyl group, each of $R^5$ and $R^6$ may be $C(O)R^7$, or each of $R^5$ and $R^6$ may be $SO_2R^8$. In some embodiments, $R^5$ may be a hydrogen atom and $R^6$ may be an alkyl group, $C(O)R^7$, or $SO_2R^8$. In other embodiments, $R^5$ may be an alkyl group, and $R^6$ may be $C(O)R^7$, or $SO_2R^8$. In still other embodiments, $R^5$ may be $C(O)R^7$, and $R^6$ may be $SO_2R^8$. When either or both of $R^5$ and $R^6$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. When each of $R^5$ and $R^6$ comprises an alkyl group, $R^5$ and $R^6$ may comprise the same alkyl group, or $R^5$ and $R^6$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

$R^7$ and $R^8$ are independently selected from the group consisting of an alkyl group, an aryl group, or an aralkyl group. When either or both of $R^7$ or $R^8$ is an alkyl group, the alkyl group may comprise about one carbon atom, more than about one carbon atom, more than about two carbon atoms, more than about four carbons atoms, more than about six carbon atoms, more than about eight carbon atoms, or more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, less than about twenty-two carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. In compounds of Formula I or pharmaceutically acceptable salts thereof, when both $R^7$ and $R^8$ groups are present, and when each of $R^7$ and $R^8$ comprises an alkyl group, $R^7$ and $R^8$ may comprise the same alkyl group, or $R^7$ and $R^8$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

When either or both of $R^7$ or $R^8$ are an aryl group, the aryl group may comprise one arene ring or more than one arene ring. Arene rings may comprise up to six carbon atoms, up to eight carbon atoms, up to ten carbon atoms, up to twelve carbon atoms, up to fourteen carbon atoms, up to sixteen carbon atoms, or up to eighteen carbon atoms. Arene rings may comprise a heteroatom, for example, nitrogen, oxygen, or sulfur. If more than one arene ring is present in an aryl group, the arene rings may be fused together, or they may be joined by a chemical bond. In compounds of Formula I or pharmaceutically acceptable salts thereof, when both $R^7$ and $R^8$ groups are present, and when each of $R^7$ and $R^8$ comprises an aryl group, $R^7$ and $R^8$ may comprise the same aryl group, or $R^7$ and $R^8$ may comprise different aryl groups. Non-limiting examples of aryl groups include substituted and unsubstituted phenyl, 1-naphthyl, 2-naphthyl, 9-anthracenyl, and biphenyl.

When either or both of $R^7$ or $R^8$ are an aralkyl group, the aralkyl group may comprise one arene ring or more than one arene ring. The aralkyl group may comprise up to six carbon atoms, up to eight carbon atoms, up to ten carbon atoms, up to twelve carbon atoms, up to fourteen carbon atoms, up to sixteen carbon atoms, up to eighteen carbon atoms, or up to twenty carbon atoms. If more than one arene ring is present in the aralkyl group, the arene rings may be fused together, or they may be joined by a chemical bond. Arene rings may comprise a heteroatom, for example, nitrogen, oxygen, or sulfur. In compounds of Formula I or pharmaceutically acceptable salts thereof, when both $R^7$ and $R^8$ groups are present, and when each of $R^7$ and $R^8$ comprises an aralkyl group, $R^7$ and $R^8$ may comprise the same aralkyl group, or $R^7$ and $R^8$ may comprise different aralkyl groups. Non-limiting examples of aralkyl groups include benzyl, 1-phenylethyl, 2-phenylethyl, 3-phenylpropyl, 2-naphthylethyl, and 9-anthracenylmethyl.

In some embodiments, $R^1$ is $NR^5R^6$, where $R^5$ and $R^6$ are each a hydrogen atom, and $R^2$, $R^3$, and $R^4$ are each OH. In some embodiments, pharmaceutically acceptable salts are selected from ammonium chlorides and ammonium sulfates. In some embodiments, the dental composition comprises a compound of Formula II, Formula III, or Formula IV, or a pharmaceutically acceptable salt thereof. In some embodiments the salt comprises ammonium chlorides or ammonium sulfates.

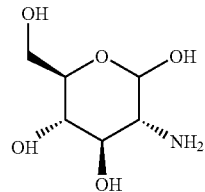

(II)

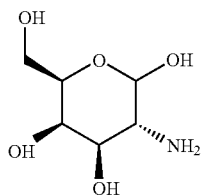

(III)

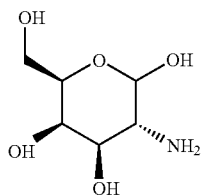

(IV)

In some embodiments, $R^1$ is $NR^5R^6$, where $R^5$ and $R^6$ are each a hydrogen atom, $R^2$ and $R^3$ are each OH, and $R^4$ is $OP(O)(OH)_2$. In a specific embodiment, the dental composition comprises a compound of Formula V or a pharmaceutically acceptable salt thereof. The pharmaceutically acceptable salt may comprise a zwitterion.

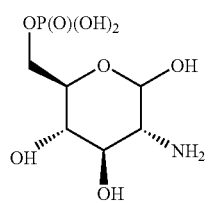

(V)

In some embodiments, $R^1$ is $NR^5R^6$, where $R^5$ is $C(O)R^7$, and where $R^7$ is an alkyl group having twelve carbon atoms, an alkyl group having fourteen carbon atoms, or an alkyl group having sixteen carbon atoms, and $R^6$ is a hydrogen atom. In specific embodiments, the dental composition comprises a compound of Formula VI, Formula VII, or Formula VIII.

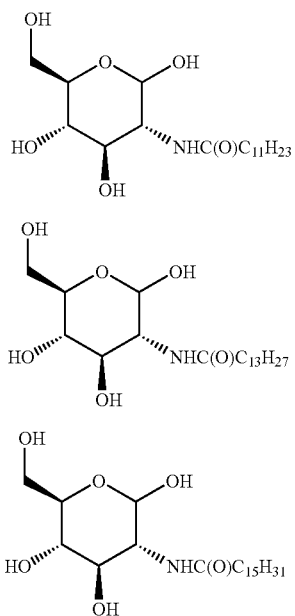

(VI)

(VII)

(VIII)

In Formulae II-VIII, the stereochemical configuration about four of the five chiral carbon atoms in each ring are specified using the conventional notation for the bonds. The stereochemical configuration about one chiral carbon atom in each ring is not specified. It is intended that Formulae II-VIII, as used in this description and in the claims, represent each of the compounds having any of the possible stereochemical configurations. Among the useful compounds are compounds having the common names D-glucosamine, D-galactosamine, D-mannosamine, D-glucosamine-6-phosphate, N-dodecanoyl-D-glucosamine, N-tetradecanoyl-D-glucosamine, and N-hexadecanoyl-D-glucosamine.

Pharmaceutically acceptable salts include ammonium salts and phosphate salts. In some embodiments, the dental composition of the invention comprises an ammonium salt. In other embodiments, the dental composition comprises a phosphate salt. In certain embodiments, the dental composition comprises an ammonium salt and a phosphate salt in the same compound or in different compounds. An ammonium salt may be represented as the reaction product of an acid with an amine, or as the reaction product of an amine with an alkylating agent such as, for example, iodomethane, bromoethane, or benzyl bromide. A phosphate salt may be represented as the reaction product of a base with a phosphate ester, wherein the phosphate ester has at least one acidic hydrogen atom.

An ammonium salt includes a protonated amine compound, for example a compound of Formula I in which a $NR^5R^6$ group, wherein $R^5$ and $R^6$ are independently selected from the group consisting of a hydrogen atom or an alkyl group, has been protonated with an inorganic acid or an organic acid.

An ammonium salt includes an alkylated amine compound, for example a compound of Formula I in which a $NR^5R^6$ group, wherein each $R^5$ and $R^6$ is selected from the group consisting of a hydrogen atom or an alkyl group, has been alkylated with an alkylating agent.

An ammonium salt comprises at least one counter ion that may be an inorganic anion, an organic anion, or a combination of anions. A combination of anions includes a combination of more than one inorganic anion, a combination of more than one organic anion, or a combination of an inorganic ion and an organic anion. Inorganic ions include, for example, fluoride, chloride, bromide, iodide, nitrate, sulfate, tetrafluroborate, and tetra(aryl)borates. Tetra(aryl)borates include compounds having the formula $Z_4B^-$, where Z is an aromatic group, for example a substituted or unsubstituted phenyl group. Examples of tetra(aryl)borates include, but are not limited to, tetraphenylborate, tetrakis(4-methylphenyl)borate, tetrakis(2-methylphenyl)borate, tetrakis(1,3,5-trimethylphenyl)borate, tetrakis(4-fluorophenyl)borate, tetrakis(pentafluorophenyl)borate, and tetrakis(4-trifluoromethylphenyl)borate. Organic anions include, for example, alkanoates (such as, for example, acetate, propionate, and butanoate), benzoate, fumarate, maleate, tartrate, ascorbate, benzenesulfonate, toluenesulfonate, and citrate. In some embodiments, organic ions may comprise substituted or unsubstituted tropolone.

In one aspect, an ammonium salt may be formed by protonation of a compound of Formula I, wherein $R^5$ and $R^6$ are independently selected from the group consisting of a hydrogen atom and an alkyl group, with an inorganic acid, an organic acid, or a combination of an inorganic acid and an organic acid. In another aspect, an ammonium salt may be formed by alkylation of a compound of Formula I, wherein $R^5$ and $R^6$ are independently selected from the group consisting of a hydrogen atom and an alkyl group, with an alkylating agent. In yet another aspect, an ammonium salt may be formed by an ion exchange or metathesis reaction with a previously formed ammonium salt.

A phosphate salt may comprise a deprotonated phosphate ester compound, for example a compound of Formula I in which a $OP(O)(OH)_2$ group has been deprotonated with a base. The base may be an inorganic base, an organic base, or a combination of an inorganic base and an organic base. A phosphate salt comprises at least one counter ion that may be a metal cation, a non-metal cation, or a combination of cations. A combination of cations includes a combination of more than one metal cation, a combination of more than one non-metal cation, or a combination of a metal cation and a non-metal cation. Metal cations include, for example, cations of metals of Groups 1A, 2A, 3B, 4B, 5B, 6B, 7B, 8B, 11B, 12B, and the lanthanides. Examples of metal cations include cations of lithium, sodium, potassium, magnesium, calcium, barium, iron, copper, silver, and zinc. Non-metal cations include, for example, ammonium cations and phosphonium cations. Ammonium and phosphonium cations may comprise alkyl, aralkyl, or aryl groups. Examples of non-metal cations include ammonium, monoalkylammonium, dialkylammonium, trialkylammonium, tetraalkylammonium, monoarylammonium, diarylammonium, triarylammonium, tetraarylammonium, and tetraarylphosphonium cations.

In one aspect, a phosphate salt may be formed by deprotonation of a OP(O)(OH)2 group in a compound of Formula I with at least one base. In another aspect, a phosphate salt may be formed by an ion exchange or metathesis reaction with a previously formed phosphate salt.

In some embodiments, the dental composition comprises a compound comprising both an ammonium salt and a phosphate salt. In some embodiments, a compound comprising both an ammonium salt and a phosphate salt may comprise a zwitterion, i.e., a compound having a cation and an anion in the same molecule.

The dental composition may comprise an amount of a compound of Formula I, or a pharmaceutically acceptable salt thereof, sufficient to inhibit formation of a biofilm. In some embodiments, the dental composition may comprise an amount of a compound of Formula I sufficient to inhibit the formation of a biofilm in the oral cavity of a subject. In some embodiments, the dental composition may comprise an amount of a compound of Formula I sufficient to inhibit the formation of a biofilm on a hard surface in the oral cavity of a subject. In some embodiments, the hard surface may comprise a tooth. In some embodiments the dental composition may comprise an amount of a compound of Formula I sufficient to inhibit the formation of a biofilm on a dental restoration. The dental composition may contain up to about forty weight percent, up to about thirty weight percent, up to about twenty weight percent, up to about sixteen weight percent, up to about twelve weight percent, up to about ten weight percent, up to about six weight percent, up to about four weight percent, up to about two weight percent, or up to about one weight percent of a compound of Formula I, based on the combined weights of the compound, the binder, and any additives such as a pharmaceutically acceptable carrier, a flavoring agent, or a coloring agent. The dental composition may comprise less than about ten weight percent, less than about five weight percent, less than about two weight percent, less than about one weight percent, less than about 0.6 weight percent, less than about 0.4 weight percent, less than about 0.2 weight percent, or less than about 0.1 weight percent of a compound of Formula I, based on the combined weights of the compound, the binder, and any additives such as a pharmaceutically acceptable carrier, a flavoring agent, or a coloring agent.

In some embodiments, the dental composition may comprise a concentration of a compound of Formula I, or a pharmaceutically acceptable salt thereof, up to about 0.5 molar, up to about 0.3 molar, up to about 0.15 molar, up to about 0.1 molar, up to about 0.05 molar, up to about 0.03 molar, up to about 0.02 molar, or up to about 0.01 molar. In certain embodiments, the dental composition may comprise a concentration of a compound of Formula I, or a pharmaceutically acceptable salt thereof, up to about the solubility limit of the compound, or a pharmaceutically acceptable salt thereof, in a binder or in a pharmaceutically acceptable carrier. In other embodiments, the dental composition may comprise a concentration of a compound of Formula I, or a pharmaceutically acceptable salt thereof, greater than about the solubility limit of the compound, or a pharmaceutically acceptable salt thereof, in a binder or in a pharmaceutically acceptable carrier.

In some embodiments, the dental composition may provide a concentration of a compound of Formula I, or a pharmaceutically acceptable salt thereof, up to about the solubility limit of the compound, or a pharmaceutically acceptable salt thereof; in a medium such as, for example, water, culture broth, or saliva. In certain embodiments, the dental composition may provide a concentration of a compound of Formula I, or a pharmaceutically acceptable salt thereof, less than the solubility limit of the compound, or a pharmaceutically acceptable salt thereof, in a medium such as, for example, water, culture broth, or saliva. It is recognized that the solubility limit may be different in different media. As used herein, the term "provide a concentration" of a compound of Formula I, or a pharmaceutically acceptable salt thereof, refers to a property of the dental composition to release or transfer to a medium such as, for example, water, culture broth, or saliva an amount of a compound, or a salt thereof, resulting in a concentration of the compound, or a salt thereof, in the medium. In some embodiments, the dental composition may provide a concentration of a compound of Formula I, or a pharmaceutically acceptable salt thereof, up to about 0.5 molar, up to about 0.3 molar, up to about 0.15 molar, up to about 0.1 molar, up to about 0.05 molar, up to about 0.03 molar, up to about 0.02 molar, up to about 0.01 molar, up to about 0.005 molar, up to about 0.002 molar, or up to about 0.001 molar in a medium. In certain embodiments, the dental composition may provide a concentration of a compound of Formula I, or a pharmaceutically acceptable salt thereof, up to about the solubility limit of the compound, or a pharmaceutically acceptable salt thereof, in a medium.

The dental composition may be in contact with a surface in the oral cavity for a time sufficient to inhibit biofilm formation in the oral cavity. The time may be up to about one second, up to about five seconds, up to about ten seconds, up to about thirty seconds, up to about one minute, up to about two minutes, up to about five minutes, up to about ten minutes, up to about fifteen minutes, up to about thirty minutes, or up to about sixty minutes. The time may be less than about one month, less than about two weeks, less than about one week, less than about twenty-four hours, less than about twenty hours, less than about sixteen hours, less than about twelve hours, less than about ten hours, less than about eight hours, less than about six hours, less than about four hours, or less than about two hours.

The dental composition may comprise an amount of a compound of Formula I, or a pharmaceutically acceptable salt thereof, sufficient to inhibit formation of a biofilm comprising at least one species of bacteria found in the oral cavity of a subject. In some embodiments, the subject is a human. In other embodiments, the subject is a non-human animal The bacteria include, for example, *Streptococcus mutans* and *S. sanguis*.

Binders

The dental composition of the invention comprises a binder. The binder may provide a reservoir of a composition comprising a compound of Formula I, or a pharmaceutically acceptable salt thereof, in an oral cavity of a subject. The composition may be released from the binder. The binder may hold a composition comprising a compound of Formula I, or a pharmaceutically acceptable salt thereof, on or near a surface in an oral cavity of a subject such that, for example, the surface may be exposed to the composition. The surface may be a hard surface, e.g., that comprises a tooth. The surface may be a dental restoration. The binder may comprise an addition polymer, a condensation polymer, or a combination of an addition polymer and a condensation polymer. In some embodiments, the binder comprises at least one of an acrylic polymer, an acrylamide polymer, a vinyl polymer, an epoxy polymer, a polyurea, a polyester, a polyanhydride, a polysiloxane, or a polyurethane. In certain embodiments, the binder comprises a film forming polymer.

In some embodiments, the binder comprises an acrylic polymer. Suitable acrylic polymers include polymers and copolymers of lower alkyl esters of acrylic or methacrylic acids. In this context, the term "lower alkyl" means a straight chain, cyclic, or branched alkyl group comprising about one to about eight carbon atoms. Examples of lower alkyl esters of acrylic or methacrylic acid include methyl acrylate, ethyl acrylate, propyl acrylate, butyl acrylate, isobutyl acrylate, tert-butyl acrylate, pentyl acrylate, neopentyl acrylate, hexyl acrylate, cyclohexyl acrylate, heptyl acrylate, cyclohexylmethyl acrylate, octyl acrylate, 2-ethylhexyl acrylate, isooctyl acrylate, methyl methacrylate, ethyl methacrylate, propyl methacrylate, butyl methacrylate, isobutyl methacrylate, tert-butyl methacrylate, pentyl methacrylate, neopentyl methacrylate, hexyl methacrylate, cyclohexyl methacrylate, heptyl methacrylate, cyclohexylmethyl methacrylate, octyl methacrylate, 2-ethylhexyl methacrylate, and isooctyl methacrylate.

Acrylic polymers may comprise at least one higher alkyl ester of acrylic or methacrylic acid. In this context, the term "higher alkyl" means a straight chain, cyclic, or branched alkyl group comprising more than about eight carbon atoms. Examples of higher alkyl esters of acrylic or methacrylic acid include decyl acrylate, dodecyl acrylate, tetradecyl acrylate, hexadecyl acrylate, octadecyl acrylate, behenyl acrylate, decyl methacrylate, dodecyl methacrylate, tetradecyl methacrylate, hexadecyl methacrylate, octadecyl methacrylate, and behenyl methacrylate.

Acrylic polymers may comprise at least one monomer having, for example, an acid group, a hydroxyl group, or an amino group. Non-limiting examples of such monomers include acrylic acid, methacrylic acid, 2-hydroxyethyl methacrylate, and 2-dimethylaminoethyl methacrylate.

Acrylic polymers may comprise at least one monomer having at least one ionic group. The ionic group may have a positive charge or a negative charge, or both a positive and a negative charge. Ionic groups include, for example, carboxylate groups, sulfonate groups, ammonium groups, and phosphonium groups.

Acrylic polymers may comprise at least one macromonomer. As used herein, the term "macromonomer" refers to an oligomer or a polymer comprising at least one polymerizable group. The macromonomer may be derived from, for example, methyl methacrylate or styrene. Exemplary macromonomers include methacrylate terminated poly(styrene) and poly(ethylene glycol) methyl ether methacrylate, available from Sigma-Aldrich Co., St. Louis, Mo. Acrylic polymers may comprise at least one silicone macromonomer, for example, a silicone macromonomer having dimethylsiloxane repeating units. Exemplary silicone macromonomers include vinyl terminated poly(dimethylsiloxane) and monoglycidyl ether terminated poly(dimethylsiloxane), available from Sigma-Aldrich Co., St. Louis, Mo.

Acrylic polymers may comprise at least one monomer comprising a fluorocarbon group. The fluorocarbon group may comprise a fluoroalkyl group, which may be a straight chain, branched or cyclic fluoroalkyl group. The fluorocarbon group may comprise a perfluoroalkyl group, which may be a straight chain, branched or cyclic perfluoroalkyl group. The fluorocarbon group may comprise a fluoroaryl group. The fluorocarbon group may comprise a perfluoroaryl group.

In some embodiments, the binder may comprise a reactive polymer. As used herein, the term "reactive polymer" refers to a polymer comprising at least one reactive group, i.e., a group that can react to form a covalent or ionic bond with a counterpart group on the same polymer chain, on another polymer chain (e.g., form a crosslink), on a different polymer, or on a surface. A surface may include a surface in the oral cavity of a subject, for example, a surface of a tooth. Examples of reactive groups include ionic groups, isocyanate groups, alkoxysilane groups, halosilane groups, acylsilane groups, ethylenically unsaturated groups (e.g., acrylate groups, methacrylate groups, and vinyl groups), epoxy groups, hydroxy groups, amino groups, ammonium groups, carboxy groups, carboxylate groups, azlactone groups, and anhydride groups.

In some embodiments, the binder may comprise a non-reactive polymer. As used herein, the term "non-reactive polymer" refers to a polymer that is substantially free of reactive groups, i.e., substantially free of groups that can react to form a covalent or ionic bond with counterpart groups on the same or another polymer chain or on a surface.

In some embodiments, the binder may comprise a hydrogel. The hydrogel may comprise a thermally responsive hydrogel, i.e., a hydrogel that undergoes a physical change in response to a change in temperature. Exemplary hydrogel binders are disclosed, for example, in U.S. Pat. No. 6,620,405 (Oxman et al.), U.S. Pat. No. 7,223,826 (Ali, et al.), and in U.S. Patent Publication No. 2004/0151691 (Oxman et al.).

Exemplary binders are disclosed in, for example, U.S. Pat. No. 5,130,347 (Mitra), U.S. Pat. No. 5,525,648 (Aasen et al.), U.S. Pat. No. 5,607,663 (Rozzi et al.), U.S. Pat. No. 5,662,887 (Rozzi et al.), U.S. Pat. No. 5,725,882 (Kumar et al.), U.S. Pat. No. 5,866,630 (Mitra et al.), U.S. Pat. No. 5,876,208 (Mitra et al.), U.S. Pat. No. 5,888,491 (Mitra et al.), U.S. Pat. No. 6,312,668 (Mitra et al.) and U.S. Pat. Publication No. 2004/0185013 (Burgio et al.). In certain embodiments, the binder comprises a repeating unit that includes a fluoride releasing group. Fluoride releasing groups include tetrafluoroborate anions and are disclosed in, for example, U.S. Pat. No. 4,871,786 (Aasen et al.).

Exemplary polysiloxane binders are disclosed in, for example, U.S. Pat. No. 5,468,477 (Kumar et al.). In some embodiments, the polysiloxanes are dispersible in water. In certain embodiments, water-dispersible siloxane polymers include those functionalized with pendant moieties that include, for example, carboxylic acid groups, including dicarboxylic acid groups.

In some embodiments, the binder may be soluble in a pharmaceutically acceptable carrier or solvent. In some embodiments, the binder may be dispersible in a pharmaceutically acceptable carrier or solvent. In some embodiments, the binder may be a latex or emulsion, e.g., a latex or emulsion in which the carrier or the continuous phase comprises water. In certain embodiments, the latex or emulsion may comprise a self-emulsifying binder. In certain embodiments, the latex or emulsion may comprise a surfactant.

Pharmaceutically Acceptable Carrier

The dental composition of the invention may comprise a pharmaceutically acceptable carrier. The pharmaceutically acceptable carrier may comprise a liquid, a solid, or both. In some embodiments, the carrier may be a liquid at about room temperature. In other embodiments, the carrier may be a solid at about room temperature. In some embodiments, the carrier may be a liquid at about the temperature of the oral cavity of a human, i.e., at about 37° C. In other embodiments, the carrier may be a solid at about the temperature of the oral cavity of a human. Exemplary liquid carriers include water, alcohols (e.g., ethanol), glycerol, sorbitol, and liquid silicones. Exemplary solid carriers include polymers such as natural rubber, butyl rubber, poly(isobutylene), elastomers, styrene-butadiene rubber, polysaccharides, and waxes (e.g., beeswax).

Each non-carrier component of the dental composition may independently be dissolved, dispersed, suspended, or emulsified in the carrier. In some embodiments, at least one component of the dental composition is dissolved in the carrier. In some embodiments, at least one component of the dental composition is dispersed in the carrier. In some embodiments, at least one component of the dental composition is suspended in the carrier. In some embodiments, at least one component of the dental composition is emulsified in the carrier.

Additives

In some embodiments, the dental composition comprises a flavoring agent. In some embodiments, the flavoring agent includes an agent that imparts a flavor, e.g., a mint flavor, to the dental composition. In some embodiments, the flavoring agent includes an agent that imparts a tactile sensation, e.g., a cooling sensation, to the dental composition. The flavoring agent may be dissolved, dispersed, suspended, or emulsified in the dental composition. In some embodiments wherein the dental composition comprises a carrier, the flavoring agent may be dissolved, dispersed, suspended, or emulsified in the carrier.

In some embodiments, the dental composition comprises a coloring agent. The coloring agent can be any dye or pigment. The coloring agent may be dissolved, dispersed, suspended, or emulsified in the dental composition. In some embodiments wherein the dental composition comprises a carrier, the coloring agent may be dissolved, dispersed, suspended, or emulsified in the carrier.

In some embodiments, the dental composition further comprises an additive having a therapeutic property. The therapeutic property may include, for example, antiplaque activity, anticaries activity or antimicrobial activity. In some embodiments, the additive having a therapeutic property may be a pharmaceutically acceptable carrier such as, for example, ethanol. Examples of additives having anticaries activity include, for example, fluoride sources such as sodium fluoride and stannous flouride. Examples of additives having antimicrobial activity include glycerol esters of fatty acids (e.g., glyceryl monolaurate), salts of chlorhexidene (e.g., chlorhexidene gluconate), long chain alkyl ammonium or pyridinium salts (e.g., cetylpyridinium chloride), hydrogen peroxide, stannous fluoride, and triclosan. In some embodiments, the additive may have biofilm inhibiting or biofilm disrupting activity. The additive may be an enzyme (e.g., dextranase). The additive may be an essential oil. The additive may be a polymer. The additive may be a compound described in U.S. Provisional Application No. 60/951,761, filed on even date herewith.

The dental composition may have a form comprising a solution, a dispersion, a suspension, an emulsion, a solid, a paste, a foam, or a gel. Any component of the dental composition may be dissolved, dispersed, suspended, or emulsified in any other component of the dental composition. In some embodiments, the components are mutually soluble (i.e., miscible with each other).

The dental composition may be formulated by combining a compound of Formula I, or a pharmaceutically acceptable salt thereof, with at least one other component of the composition. The compound may be combined with a pharmaceutically acceptable carrier. If the carrier is a liquid, the compound may be dissolved, dispersed, suspended, or emulsified in the carrier. If the carrier is a solid, the compound may be combined with the carrier by, for example, milling or grinding. In one aspect, a compound of Formula I, or a pharmaceutically acceptable salt thereof, may be combined with other components of the composition after the other components have been combined with each other. In another aspect, all of the components, including a compound of Formula I, or a pharmaceutically acceptable salt thereof, may be combined at the same time.

Method and Kit

In another aspect, the invention provides a method of inhibiting biofilm formation on a surface of the oral cavity of a subject, comprising the steps of (1) providing a composition comprising a compound of Formula I or a pharmaceutically acceptable salt thereof, and a binder, wherein the composition is a film forming composition, and (2) applying the composition to a surface in the oral cavity of a subject. The surface in the oral cavity of a subject includes, for example, a buccal surface, a gingival surface, a tooth, a dental restoration, and bone. The composition may be applied to the oral cavity of a subject by, for example, immersing, inserting, rinsing, spraying, brushing, swabbing, or combinations thereof. Spraying the composition may provide the composition in the form of, for example, an aerosol or a fine mist. The subject may be a human, or the subject may be a non-human animal. Non-human animals include mammals such as canines and felines.

In another aspect, the invention provides a kit comprising (1) a composition comprising a compound of Formula I or a pharmaceutically acceptable salt thereof, and a binder, wherein the composition is a film forming composition, and (2) an application accessory. The application accessory can be a container, a sprayer, a brush, a swab, a tray, and combinations thereof. The application accessory can be any size. The kit may include more than one application accessory or more than one kind of application accessory (i.e., a sprayer and a brush). The kit may also comprise instructions for using the kit.

Examples

Unless otherwise noted, all compounds and reagents were or can be obtained from Sigma-Aldrich Corp., St. Louis, Mo.

N-Acetyl-D-galactosamine was obtained from MP Biomedicals, Solon, Ohio.

beta-Gentiobiose was obtained from MP Biomedicals, Solon, Ohio.

Glucosamine sulfate was obtained from MP Biomedicals, Solon, Ohio.

Mannosamine HCl was obtained from MP Biomedicals, Solon, Ohio.

Laminaritetraose was obtained from Seikagaku Corp., Tokyo, Japan.

Galactosamine HCl was obtained from EMD Chemicals Inc., San Diego, Calif.

D-Tagatose was obtained from Alfa Aesar, Ward Hill, Mass.

N-Acetylmannosamine was obtained from Alfa Aesar, Ward Hill, Mass.

Quantitative Biofilm Inhibition Test

Compounds of the dental compositions of the invention, and comparative compounds, were evaluated for biofilm inhibition activity. Composite dental restorative (available under the trade designation "FILTEK SUPREME" from 3M ESPE Dental Products, St. Paul, Minn.) was placed in a 15 millimeter by 1 millimeter stainless steel die. The open ends of the die were then covered with polyester film and the die was subjected to a pressure of 68.95 MPa using a hydraulic press. While the die containing the composite restorative was under compression, the composite was irradiated for two minutes using a Model ACE light source (available from SCHOTT North America, Inc., Auburn, N.Y.). The discs of cured composite restorative were then further cured using a Model UniXS light box (available from Heraeus Kulzer, Inc., Armonk, N.Y.) for 1.5 minutes.

The cured discs of composite restorative were then immersed in ten milliliters of *Streptococcus mutans* culture (ATCC 25175; $10^6$ CFU/mL) prepared in brain heart infusion broth that contained 1.0 weight percent sucrose and 1 weight percent of a compound of the dental composition. The samples were incubated at 37° C. for approximately twenty hours, after which time the cured discs were removed from the broth and were gently rinsed with water. Each disc was placed in a separate test tube containing five milliliters of 1M aqueous sodium hydroxide solution, and each test tube was then sonicated for two minutes using a model SH1012-40-8 ultrasonic generator (manufactured by Branson Ultrasonics Corp., Danbury, Conn.) for two minutes to dislodge biofilm on the disc. The optical absorbance (optical density) of each aqueous sodium hydroxide solution was then measured at 550 nm using a Model ULTROSPEC III UV-visible spectrophotometer (manufactured by Pharmacia AB, Uppsala, Sweden). For each compound of the dental composition, five discs were separately incubated in broth and were evaluated separately to provide five optical density measurements. The average of the five optical density measurements was then calculated. Control or comparative samples, corresponding to each exemplary sample, were prepared essentially as described above except that the culture in brain heart infusion broth did not contain a compound of the dental composition. The average optical density of the control or comparative samples was determined as described above. The ratio, expressed as a percentage, of the average optical density for each compound sample to the average optical density for a control sample was calculated by dividing the average optical density for each compound sample by the average optical density for a control sample and multiplying the result by one hundred. The ratio was considered to be proportional to the average amount of biofilm on the five cured discs, i.e., relatively low average optical density ratio was considered to be indicative of inhibition of biofilm formation. The ratio for the control was 100%.

Qualitative Biofilm Inhibition Test

During the procedure for the Quantitative Biofilm Inhibition Test, each cured disc was visually examined after it was removed from the broth (and rinsed with water) and before it was placed in a test tube containing five milliliters of 1M aqueous sodium hydroxide solution. The presence or absence of visible biofilm on a disc was noted.

Bacterial Kill Rate Test

Compounds of the dental compositions of the invention were evaluated for extent of bacterial kill in culture. Overnight cultures of *Streptococcus mutans* in brain heart infusion broth ($10^6$ CFU/mL) was mixed with a 0.1 weight percent, 0.5 weight percent, or 1.0 weight percent aqueous solution of each compound of the dental composition. After a period of 2, 5, or 10 minutes, 1.0 mL of the mixture was transferred via pipette into a first tube containing 9.0 mL of Letheen broth to provide a $10^{-1}$ dilution. The contents of the tube were mixed using a vortex mixer. A 1.0 mL aliquot of this sample was transferred via pipette into a second tube containing 9.0 mL of Letheen broth to provide a $10^{-2}$ dilution. A 0.1 mL aliquot of each dilution was plated and spread in duplicate on sheep blood agar in Petri dishes, using a "hockey stick" applicator, to provide $10^{-2}$ and $10^{-3}$ dilutions, respectively, on each plate. The plates were incubated at 37° C. for a period of 48 to 72 hours, and then the colony forming units were counted. The CFU counts were compared and the log reduction in the counts were calculated.

Minimum Inhibitory Concentration (MIC) Test

The MIC Test was carried out using successively lower concentrations of compounds. Sterile tryptic soy broth (50 microliters; TSB, available from BD Dfico, Becton, Dickinson and Company, Franklin Lakes, N.J.) was deposited into each well of a sterile polystyrene 96-well microtiter plate. Into each well in the first (leftmost) column of the plate, there was then deposited a 50 microliter aliquot (of known concentration) of a compound (i.e., a compound of Formula I, or a pharmaceutically acceptable salt thereof, or comparative compound). A 50 microliter aliquot of the mixture in the first (leftmost) well in the first row of the plate was transferred to the second well in the first row. A 50 microliter aliquot of the mixture in the second well in the first row was then transferred to the third well in the first row. The compound was successively diluted (1:1 dilution at each step) by transferring a 50 microliter aliquot from one well into the next well, across the row of the plate. This procedure was repeated for each row of the plate. Then, an overnight culture of *Streptococcus mutans* (strain ATCC 25175) was diluted 1:100 into sterile tryptic soy broth. A 50 microliter aliquot of the diluted *S. mutans* culture ($10^5$ CFU) was deposited into each well of the microtiter plate. The plate was then incubated at 37° C. for 24 hours in a sealed humidified chamber. The plate was then visually inspected to determine the lowest concentration of compound at which no bacterial growth was visible. This value was considered to be the minimum inhibitory concentration (MIC) for the compound. The test was repeated using *Staphylococcus aureus* (strain ATCC 6538) and *Pseudomonas aeruginosa* (strain ATCC 9027) in place of *S. mutans*.

Examples 1-5 and Comparative Examples 1-12

Biofilm Inhibition

The Quantitative Biofilm Inhibition Test was carried out using five compounds of the dental composition and eleven comparative compounds, each at a concentration of 1 weight percent. A control Test was carried out on a sample (Comparative Example 1) that did not contain an exemplary or comparative compound. In addition, the Qualitative Biofilm Inhibition Test was carried out for each Example and Comparative Example, in which each disc was visually examined before it was placed in the tube containing the aqueous sodium hydroxide solution. The data are given in Table 1. In Table 1, "OD Ratio" refers to the ratio, expressed as a percentage, of the average optical density for each compound to the average optical density for a control sample, calculated by dividing the average optical density for each compound by the average optical density for a control sample and multiplying the result by one hundred; "+" refers to a visual assessment that a compound inhibited biofilm formation, and "−" refers to a visual assessment that either a compound did not inhibit biofilm formation, or that bacteria grew in the culture broth.

TABLE 1

Biofilm Inhibition Data for Examples 1-5 and Comparative Examples 1-12.

| Example | Compound | OD Ratio | Visual Assessment |
|---|---|---|---|
| 1 | Glucosamine HCl | 0% | + |
| 2 | Galactosamine HCl | 0% | + |

TABLE 1-continued

Biofilm Inhibition Data for Examples
1-5 and Comparative Examples 1-12.

| Example | Compound | OD Ratio | Visual Assessment |
|---|---|---|---|
| 3 | Glucosamine Sulfate | 2% | + |
| 4 | Mannosamine HCl | 0% | + |
| 5 | Glucosamine-6-Phosphate | 2% | + |
| Comparative 1 | NONE (Control) | 100% | − |
| Comparative 2 | Fucose | 121% | − |
| Comparative 3 | Mannose | 83% | − |
| Comparative 4 | Galactose | 87% | − |
| Comparative 5 | Lactose | 82% | − |
| Comparative 6 | Laminaritetraose | 97% | − |
| Comparative 7 | N-Acetylgalactosamine | 138% | − |
| Comparative 8 | N-Acetylglucosamine | 83% | − |
| Comparative 9 | Xylitol | 123% | − |
| Comparative 10 | beta-Gentiobiose | 124% | − |
| Comparative 11 | D-Tagatose | 145% | − |
| Comparative 12 | N-Acetylmannosamine | 51% | − |

Examples 6-9

Concentration of Compound to Inhibit Biofilm Formation

The Biofilm Inhibition Test was carried out, using four compounds of the dental composition, in broth containing 1.0, 2.5, or 5.0 weight percent sucrose and the exemplary compounds of the dental composition at a concentration of either 50 millimolar or 150 millimolar. The data are given in Table 2. In Table 2, the millimolar concentration of compound that inhibited biofilm formation is given for each concentration of sucrose. An entry of "n/t" means that the compound was not tested in broth containing the corresponding concentration of sucrose.

TABLE 2

Biofilm Inhibition Data for Examples 6-9.

| | | Concentration of Compound to Inhibit Biofilm Formation | | |
|---|---|---|---|---|
| Example | Compound | 1 wt% Sucrose | 2.5 wt% Sucrose | 5 wt% Sucrose |
| 6 | Glucosamine HCl | 50 mM | 50 mM | 50 mM |
| 7 | Glucosamine Sulfate | 50 mM | n/t | 150 mM |
| 8 | Glucosamine-6-Phosphate | 50 mM | n/t | n/t |
| 9 | Mannosamine HCl | 50 mM | 50 mM | 50 mM |

Examples 10-27

Bacterial Kill Rate

The Bacterial Kill Rate Test was carried out using the compounds listed in Table 3. The data are given in Table 3. In Table 3, the bacteria count reduction (log reduction) is the difference between the log of the initial bacteria count and the log of the bacteria count after 2, 5, and 10 minutes.

TABLE 3

Bacterial Kill Rate Data for Examples 10-27.

| Example | Compound (concentration) | Initial Bacteria Count (log) | Bacteria Count Reduction (log reduction) | | |
|---|---|---|---|---|---|
| | | | 2 min. | 5 min. | 10 min. |
| 10 | Glucosamine HCl (0.1 wt %) | 4.27 | 1.03 | 0.94 | 0.97 |
| 11 | Glucosamine HCl (0.5 wt %) | 4.27 | 0.99 | 0.98 | 0.93 |
| 12 | Glucosamine HCl (1.0 wt %) | 4.27 | 0.93 | 0.99 | 0.97 |
| 13 | Glucosamine Sulfate (0.1 wt %) | 3.88 | 0.95 | 0.75 | 0.87 |
| 14 | Glucosamine Sulfate (0.5 wt %) | 3.88 | 0.78 | 0.80 | 0.81 |
| 15 | Glucosamine Sulfate (1.0 wt %) | 3.88 | 0.95 | 0.89 | 0.97 |
| 16 | N-Acetylglucosamine (0.1 wt %) | 4.32 | 1.09 | 1.02 | 1.04 |
| 17 | N-Acetylglucosamine (0.5 wt %) | 4.32 | 1.12 | 1.16 | 0.99 |
| 18 | N-Acetylglucosamine (1.0 wt %) | 4.32 | 1.05 | 1.12 | 1.06 |
| 19 | N-Acetylmannosamine (0.5 wt %) | 3.99 | 0.93 | 1.54 | 1.61 |
| 20 | Galactosamine HCl (0.1 wt %) | 3.99 | 1.13 | 1.00 | 0.96 |
| 21 | Galactosamine HCl (0.5 wt %) | 3.99 | 0.89 | 1.08 | 1.31 |
| 22 | Mannosamine HCl (0.1 wt %) | 3.99 | 1.01 | 0.82 | 0.95 |
| 23 | Mannosamine HCl (0.5 wt %) | 3.99 | 0.96 | 0.98 | 1.00 |
| 24 | Mannosamine HCl (1.0 wt %) | 3.99 | 0.96 | 1.09 | 0.99 |
| 25 | Glucosamine-6-Phosphate (0.1 wt %) | 4.09 | 0.99 | 0.88 | 1.06 |
| 26 | Glucosamine-6-Phosphate (0.5 wt %) | 4.09 | 0.95 | 1.11 | 1.23 |
| 27 | Glucosamine-6-Phosphate (1.0 wt %) | 4.09 | 1.12 | 1.41 | 2.09 |

Examples 28-36

Binder Containing Composition

For Examples 28-30, glucosamine-6-phosphate (40.55 mg) was combined with a mixture of an acrylate polymer (1.0 g; prepared as described in Example 3B of U.S. Provisional Patent Application No. 60/754,684) and ethanol (1.0 g) to prepare a first coating solution. Three cured discs having a diameter of 17 mm and a thickness of 1 mm were prepared from a dental composite, available under the trade designation FILTEK SUPREME XT UNIVERSAL RESTORATIVE from 3M ESPE, St. Paul, Minn. Each disc was weighed and was then dipped into the coating solution.

For Examples 31-33, glucosamine-6-phosphate (57.0 mg) was combined with a polymer (0.5 g; prepared as described in Example 11 of U.S. Pat. No. 5,130,347 (Mitra)), 2-propanol (1.0 g), and water (1.0 g) to prepare a second coating solution. Three cured discs having a diameter of 17 mm and a thickness of 1 mm were prepared from a dental composite composition as described in U.S. Patent Application Publication No. 2003/0114553. Each disc was weighed and was then dipped into the coating solution.

For Examples 34-36, glucosamine-6-phosphate (57.0 mg) was combined with a polymer (0.5 g; prepared as described in Example 11 of U.S. Pat. No. 5,130,347 (Mitra)), 2-propanol (1.0 g), and water (1.0 g) to prepare a third coating solution. Three cured discs having a diameter of 17 mm and a thickness of 1 mm were prepared from a dental composite, available under the trade designation FILTEK SUPREME XT UNIVERSAL RESTORATIVE from 3M ESPE, St. Paul, Minn. Each disc was weighed and was then dipped into the coating solution.

Each dipped disc was allowed to dry in air at room temperature for approximately 12 hours, and was further dried in an oven at approximately 37° C. for approximately 12 hours. Each dried disc was then weighed. The weight of dried polymer coating on each disc was calculated as the difference in weight between the coated disc and the uncoated disc. The data are given in Table 4.

TABLE 4

Data for Examples 28-36

| Example | Initial disc weight | Coated disc weight | Weight of coating on disc |
|---|---|---|---|
| 28 | 0.4637 g | 0.4763 g | 0.0126 g |
| 29 | 0.4776 g | 0.4875 g | 0.0099 g |
| 30 | 0.4403 g | 0.4530 g | 0.0127 g |
| 31 | 0.4340 g | 0.4436 g | 0.0096 g |
| 32 | 0.4364 g | 0.4469 g | 0.0105 g |
| 33 | 0.4433 g | 0.4519 g | 0.0086 g |
| 34 | 0.4520 g | 0.4593 g | 0.0073 g |
| 35 | 0.4492 g | 0.4589 g | 0.0097 g |
| 36 | 0.4425 g | 0.44509 g | 0.0084 g |

Examples 37-45 and Comparative Examples 13-15

Minimum Inhibitory Concentration (MIC)

A sample of each of N-dodecanoyl-D-glucosamine, N-tetradecanoyl-D-glucosamine, and N-hexadecanoyl-D-glucosamine (0.100 g each) was emulsified in water (10 g) using a nonionic surfactant (0.9 g; PLURONIC F68, available from BASF Corp., Mount Olive, N.J.). A control sample was made by combining the nonionic surfactant (0.9 g) and water (10 g).

Each of the four samples was evaluated using the Minimum Inhibitory Concentration (MIC) Test described above with S. mutans, S. aureus, and P. aeruginosa. The data are given in Table 5. In Table 5, "F68" refers to the nonionic surfactant used in the Comparative Examples, and "none" means that no inhibitory activity was noted.

TABLE 5

MIC Data for Examples 37-45 and Comparative Examples 13-15.

| Example | Compound | Bacteria | MIC |
|---|---|---|---|
| Comparative 13 | F68 | S. mutans | None |
| 37 | N-dodecanoyl-D-glucosamine | S. mutans | 0.078 mg/mL |
| 38 | N-tetradecanoyl-D-glucosamine | S. mutans | 0.078 mg/mL |
| 39 | N-hexadecanoyl-D-glucosamine | S. mutans | 0.039 mg/mL |
| Comparative 14 | F68 | S. aureus | None |
| 40 | N-dodecanoyl-D-glucosamine | S. aureus | None |
| 41 | N-tetradecanoyl-D-glucosamine | S. aureus | None |
| 42 | N-hexadecanoyl-D-glucosamine | S. aureus | None |
| Comparative 15 | F68 | P. aeruginosa | None |
| 43 | N-dodecanoyl-D-glucosamine | P. aeruginosa | None |
| 44 | N-tetradecanoyl-D-glucosamine | P. aeruginosa | None |
| 45 | N-hexadecanoyl-D-glucosamine | P. aeruginosa | None |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A dental composition comprising:

a) a compound of Formula I:

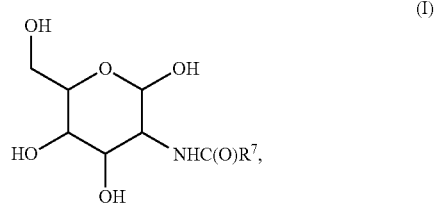

wherein $R^7$ is an alkyl group having more than about four carbon atoms and less than about twenty-two carbon atoms; and b) a binder;

wherein the binder is a film forming polymer, and wherein the dental composition is a film forming dental composition.

2. The dental composition of claim 1 wherein the compound is selected from the group consisting of

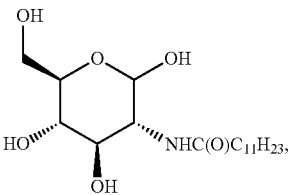
(VI)

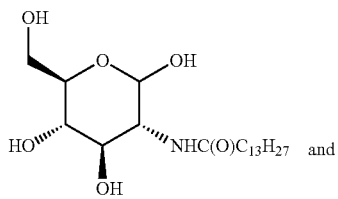 and
(VII)

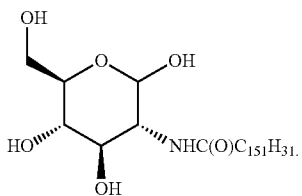
(VIII)

3. The dental composition of claim 1 further comprising a pharmaceutically acceptable carrier.

4. The dental composition of claim 3 wherein the carrier comprises ethanol.

5. The dental composition of claim 3 wherein the composition is in a form selected from the group consisting of a solution, a dispersion, a suspension, an emulsion, a solid, a paste, a foam, and a gel.

6. The dental composition of claim 1 further comprising a flavoring agent, a coloring agent, or a combination thereof.

7. The dental composition of claim 1 wherein the binder comprises at least one of an addition polymer or a condensation polymer.

8. The dental composition of claim 1 wherein the binder is selected from the group consisting of an acrylic polymer, a vinyl polymer, an epoxy polymer, a polyurea, a polyester, a polyanhydride, a polysiloxane, a polyurethane, and combinations thereof.

9. The dental composition of claim 8 wherein the binder is an acrylic polymer.

10. A method of inhibiting biofilm formation on a surface in the oral cavity of a subject, the method comprising:
   a) providing the dental composition of claim 1; and
   b) applying the composition to a surface in the oral cavity of a subject in need thereof.

11. The method of claim 10 wherein the step of applying comprises immersing, inserting, rinsing, spraying, brushing, swabbing, or combinations thereof.

12. The method of claim 10 wherein the surface is a hard surface.

13. The method of claim 12 wherein the hard surface comprises a tooth.

14. The method of claim 10 wherein the subject is selected from a human and a non-human animal.

15. A kit comprising:
   a) a dental composition of claim 1; and
   b) at least one application accessory selected from the group consisting of a container, a sprayer, a brush, a swab, a tray, and combinations thereof.

* * * * *

UNITED STATES PATENT AND TRADEMARK OFFICE
CERTIFICATE OF CORRECTION

PATENT NO. : 8,329,674 B2
APPLICATION NO. : 12/594988
DATED : December 11, 2012
INVENTOR(S) : Jie Yang et al.

It is certified that error appears in the above-identified patent and that said Letters Patent is hereby corrected as shown below:

First page, Column 2, Other Publications
Line 9, Delete "germentation" and insert -- fermentation --, therefor.
Line 30, Delete "Strptococcus" and insert -- Streptococcus --, therefor.

Page 2, Column 1, Other Publications
Line 4, Delete "SStudies," and insert -- Studies, --, therefor.
Line 15, Delete "toSaliva" and insert -- to Saliva --, therefor.

Column 1
Line 8, After "This" delete "application".

Column 5
Line 22, Delete "cyclopenyl," and insert -- cyclopentyl, --, therefor.
Line 49-50, Delete "cyclopenyl," and insert -- cyclopentyl, --, therefor.

Column 8
Line 22-23, Delete "tetrafluroborate," and insert -- tetrafluoroborate, --, therefor.

Column 13
Line 37, Delete "flouride." and insert -- fluoride. --, therefor.
Line 39, Delete "chlorhexidene" and insert -- chlorhexidine --, therefor.
Line 40, Delete "chlorhexidene" and insert -- chlorhexidine --, therefor.

Column 16
Line 6, Delete "microtiter" and insert -- microtiter --, therefor.

Column 18
Line 14, Delete "N-Acctylmannosaminc" and insert -- N-Acetylmannosamine --, therefor.

Signed and Sealed this
Twelfth Day of February, 2013

Teresa Stanek Rea
*Acting Director of the United States Patent and Trademark Office*

CERTIFICATE OF CORRECTION (continued)
U.S. Pat. No. 8,329,674 B2

Column 21
Line 22-29, In Claim 2, delete " 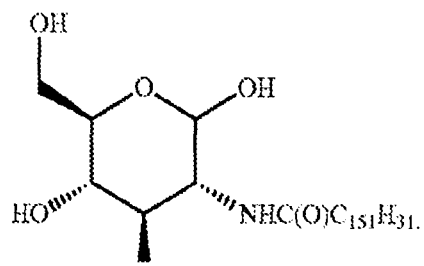 " and insert -- 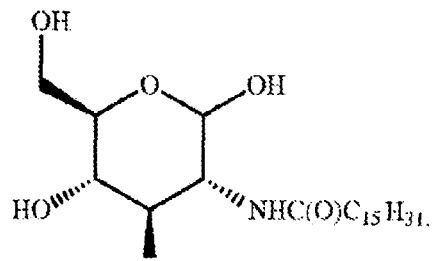 --, therefor.